United States Patent
Mizoguchi et al.

(10) Patent No.: US 6,397,659 B1
(45) Date of Patent: Jun. 4, 2002

(54) METHOD FOR DETECTING AN ELEMENT RESISTANCE OF A GAS CONCENTRATION SENSOR AND GAS CONCENTRATION DETECTION APPARATUS

(75) Inventors: Tomomichi Mizoguchi, Nagoya; Masayuki Takami, Kariya, both of (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/270,754

(22) Filed: Mar. 17, 1999

(30) Foreign Application Priority Data

Mar. 20, 1998 (JP) .......................................... 10-072369

(51) Int. Cl.$^7$ ........................ G01N 33/497; G01N 19/10
(52) U.S. Cl. ........................................ 73/23.2; 73/23.32
(58) Field of Search ............................. 73/23.32, 117.3, 73/27 R

(56) References Cited

U.S. PATENT DOCUMENTS

| 4,626,338 A | 12/1986 | Kondo et al. | |
|---|---|---|---|
| 6,067,841 A | * | 5/2000 | Suzuki et al. ............... 73/23.32 |

FOREIGN PATENT DOCUMENTS

| EP | 0 822 326 A2 | 4/1998 |
|---|---|---|
| GB | 2308452 A | 6/1997 |
| GB | 2310725 A | 9/1997 |
| JP | 59-217150 | 12/1984 |

OTHER PUBLICATIONS

U.S. application Ser. No. 09/218,083, Hasegawa, filed Dec. 22, 1998.

U.S. application Ser. No. 09/038,005, Takami, filed Mar. 11, 1998.

* cited by examiner

*Primary Examiner*—Max Noori
*Assistant Examiner*—Maurice Stevens
(74) *Attorney, Agent, or Firm*—Nixon & Vanderhye P.C.

(57) ABSTRACT

A/F ratio sensor includes an element portion using a solid electrolytic layer, and generates a sensor current in proportion to an oxygen concentration in an exhaust gas when a voltage is applied thereto. A bias control circuit switches the voltage applied to the A/F ratio sensor to an element resistance detection voltage during an element resistance detection with a given time constant, and detects the sensor current flowing at that time. A comparing circuit detects an amount of voltage change reaching a given value. A timing decision circuit decides a detection of voltage and current changes during the decision timing of the comparing circuit. A data output circuit measures the current change relative to the voltage change in response to the timing decision of the timing decision circuit. In this apparatus, the voltage change and the current change are detected when the applied voltage, which change with the given time constant, reaches to the given reference voltage Vref. In other words, the amount of the current change $\Delta I$ of the sensor current is detected before the voltage, which change with the given time constant, converges to the voltage $V_0$.

11 Claims, 9 Drawing Sheets

FIG. 5
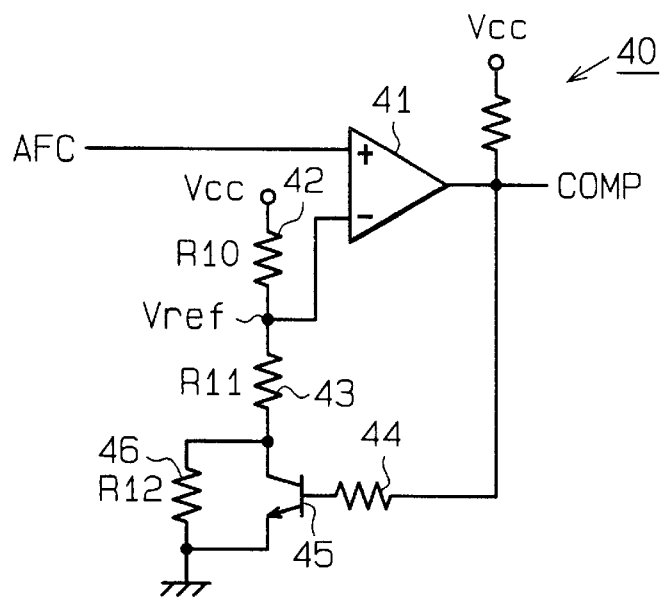
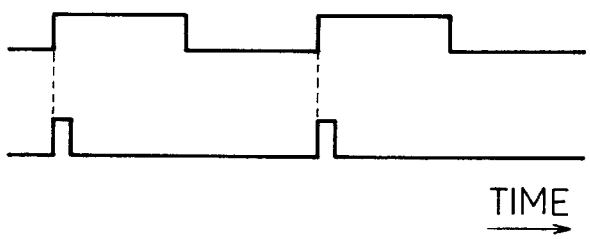
FIG. 7A  OSCILLATOR OUTPUT
FIG. 7B  ONE-SHOT CIRCUIT OUTPUT
TIME

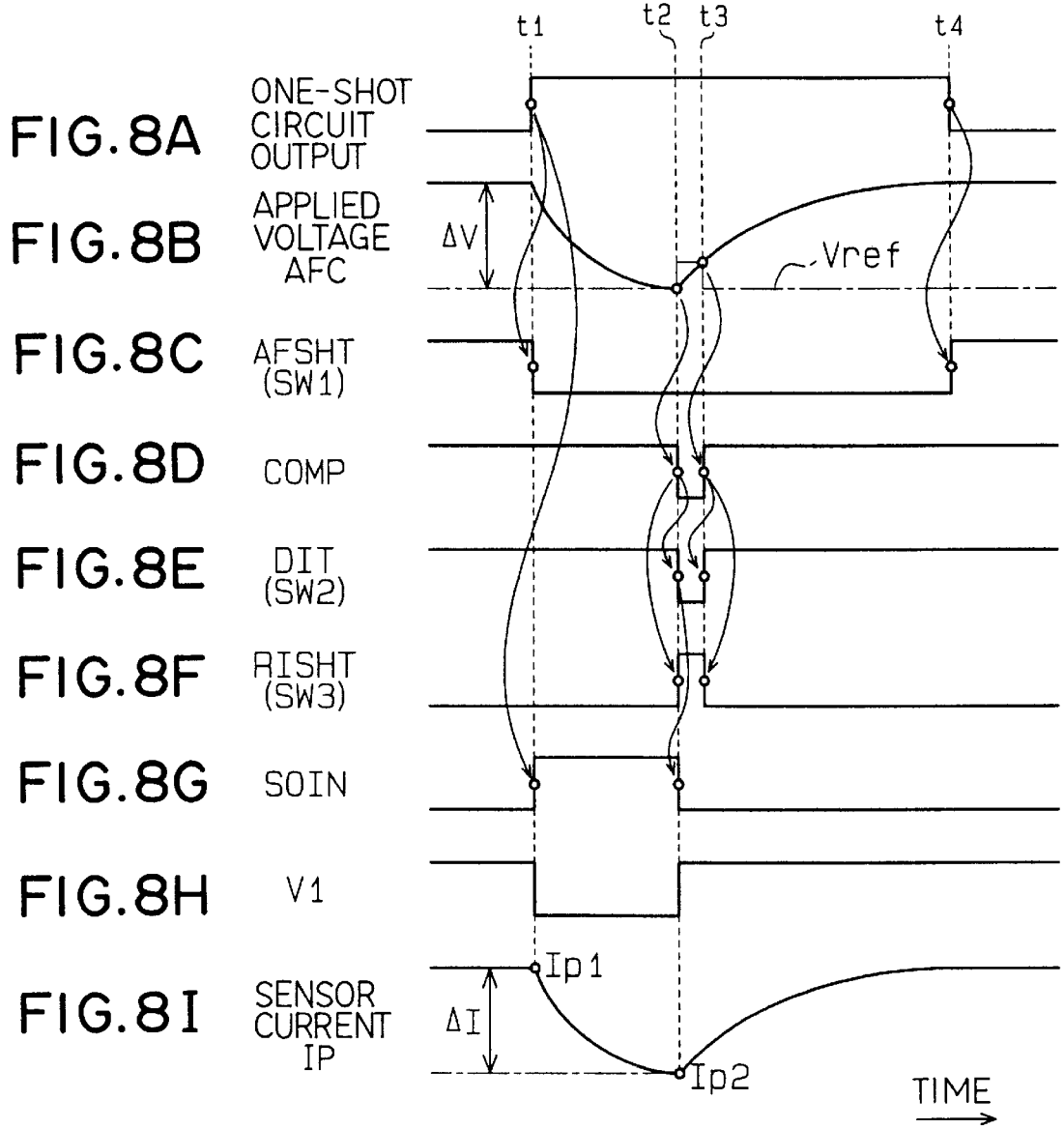

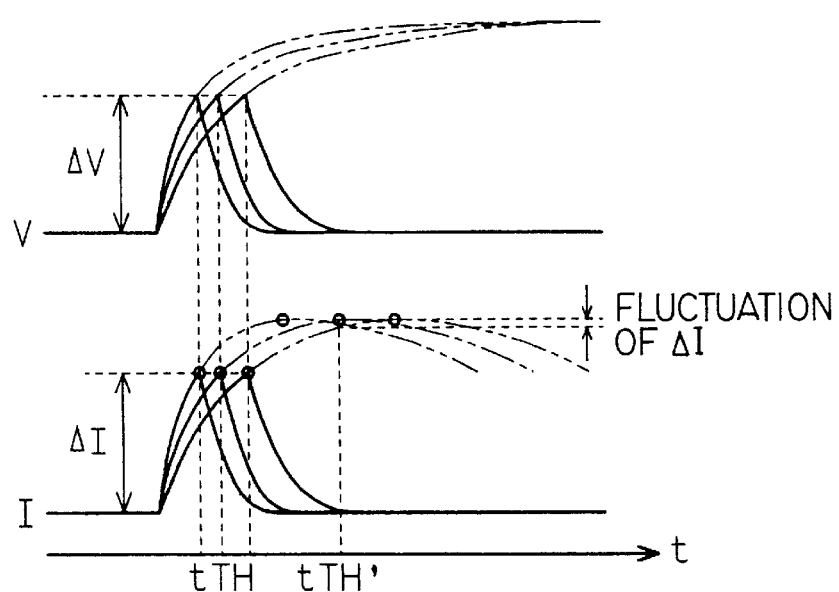
FIG.11A
FIG.11B
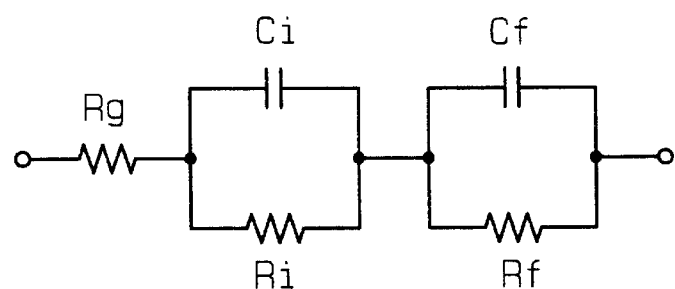
FIG.12
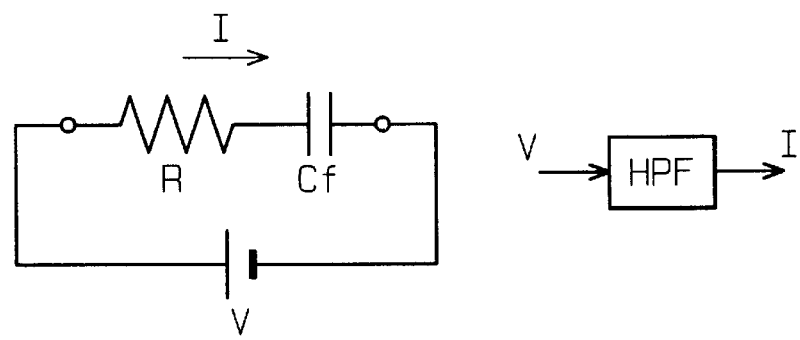
FIG.13A      FIG.13B
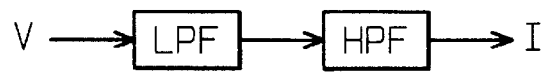
FIG.14

METHOD FOR DETECTING AN ELEMENT RESISTANCE OF A GAS CONCENTRATION SENSOR AND GAS CONCENTRATION DETECTION APPARATUS

CROSS-REFERENCE TO RELATED APPLICATION

This application is based upon and claims priority from Japanese Patent Application No. Hei. 10-72369 filed Mar. 20, 1998, the contents of which is incorporated herein by reference.

BACKGROUND OF THE INVENTION

1. Field of the Invention

The present invention relates to a gas concentration sensor for detecting a concentration of a specific constituent in a detected gas, for example, oxygen concentration in an exhaust gas from a vehicle engine, and specifically, to a method and apparatus for detecting element resistance of the gas concentration sensor.

2. Description of Related Art

A conventional oxygen concentration sensor (i.e., a limit current air-fuel ratio sensor) detects an oxygen concentration in exhaust gas from a vehicle engine. This sensor outputs a current signal relative to the oxygen concentration in the exhaust gas when a voltage is applied thereto. As to this gas concentration sensor, it needs to detect an internal resistance of the solid electrolytic (element resistance) accurately to detect its activation state or deterioration state.

FIGS. 10A and 10B are waveforms of voltage change and current change according to a conventional element resistance detection procedure of the gas concentration sensor, as disclosed in, for example, Japanese Laid-open patent application No. Hei. 9-292364. As shown in FIG. 10A, first, a voltage having a given time constant is applied to the gas concentration sensor. Next, a peak current ΔI', which is an amount of current change, is detected after passing tTH' time. The element resistance is detected based on the peak current ΔI' and a voltage ΔV' which is an amount of voltage change during tTH' time. The element resistance corresponds to (ΔV'/ΔI'). In this detection procedure, the voltage applied to the sensor change with respect to the given time constant so that a generation of excessive peak current can be prevented. Therefore, this sensor can detect both a sensor current an element resistance of sensor.

However, detection of the element resistance may fluctuate due to variation of an element resistance detection parameter, such as a fluctuation of the time constant of the voltage applied to the sensor. A mechanism of the above is explained hereinafter with reference to FIGS. 11A, 11B. As represented by the two-dot chain line in FIGS. 11A, 11B, a changing speed of the voltage fluctuates unexpectedly when the time constant of the voltage fluctuates. In this situation, a time required to reach to the peak current ΔI' also fluctuates. Then, the current detected after the tTH' time may not always reach to the peak current ΔI'. As a result, an accuracy of element resistance detection decreases.

SUMMARY OF THE INVENTION

In order to solve the foregoing problem, the present invention provides an element resistance detection procedure of a gas concentration sensor that detects an element resistance accurately even if some parameters, such as a time constant or a detection timing of current change due to voltage change, fluctuates. The present invention also aims to provide a gas concentration detection apparatus which employs the above element resistance detection procedure.

More particularly, the element resistance detection procedure of the present invention is characterized in that timings for detecting the voltage change and current change are set before the voltage, which having a given time constant, converges to a constant value. Also, the detection procedure of the present invention can detect the element resistance accurately even if some parameters, such as the time constant or the detection timing of the current change due to the voltage change, fluctuates.

The gas concentration detection apparatus of the present invention includes a first circuit to detect whether an amount of a voltage having a given time constant reaches a given value, a second circuit to determine a detection of voltage change and current change used for an element resistance detection, at the time of detection of the first circuit, and a third circuit to detect the current change in relation to the voltage change.

The gas concentration detection apparatus can detect the element resistance accurately even if some parameters, such as the time constant or the detection timing of the current change due to the voltage change, fluctuates. Since this apparatus is formed by electric circuits (i.e., the first, second and third circuit), a timing which the amount of the voltage change reaches the given value can be detected accurately.

In other words, in an engine control microcomputer (i.e., engine control ECU), operation programs are executed at a given cycle, and various other programs are executed. Therefore, the detection timing of the voltage change and the current change may fluctuate by at least 10 μs, and the detected element resistance may include some errors.

On the other hand, according to the present invention, the voltage change and the current change can be detected instantly at a desired timing, and fluctuation of the detection timing of the voltage change and the current change can be decreased substantially. Consequently, the element resistance can be detected accurately. Furthermore, since the voltage change and the current change are instantly detected, the detection impossible period of the gas concentration (i.e., A/F) can be decreased.

BRIEF DESCRIPTION OF THE DRAWINGS

The present invention will be understood more fully from the detailed description given hereinafter, taken in conjunction with the accompanying drawings.

In the drawings:

FIG. 5 is an electric circuit diagram showing a comparing circuit;

FIGS. 7A, 7B are waveforms of the output from the oscillator and the one-shot pulse circuit, respectively;

FIGS. 8A–8I are timing diagrams for explaining the operation of the embodiment;

FIGS. 11A, 11B are waveform diagrams illustrating voltage change and current change at the time of element resistance detection;

FIG. 12 is an equivalent circuit of the gas concentration sensor;

FIGS. 13A, 13B represent an equivalent circuit of the gas concentration sensor and a schematic diagram corresponding to the equivalent circuit; and FIG. 14 is a block diagram circuit configuration from the voltage command to sensor current output.

DETAILED DESCRIPTION OF THE PREFERRED EMBODIMENTS

A preferred embodiment of the present invention is explained hereinafter with reference to the accompanying drawings. In this embodiment, the present invention is applied to an air-fuel ratio detection apparatus. This air-fuel detection apparatus, which is applied to an engine that is installed in a vehicle, detects an engine air-fuel ratio (A/F) based on a limit current that flows in an A/F ratio sensor when a given voltage is applied to the A/F ratio sensor. The A/F ratio sensor is a limit current air-fuel ratio sensor that generates a limit current related to an oxygen concentration in an exhaust gas. The A/F ratio sensor also detects an element resistance based on voltage change and current change when a voltage applied to the A/F ratio sensor is temporally switched from an air-fuel ratio detection voltage (A/F detection voltage) to an element resistance detection voltage.

Figure 1:
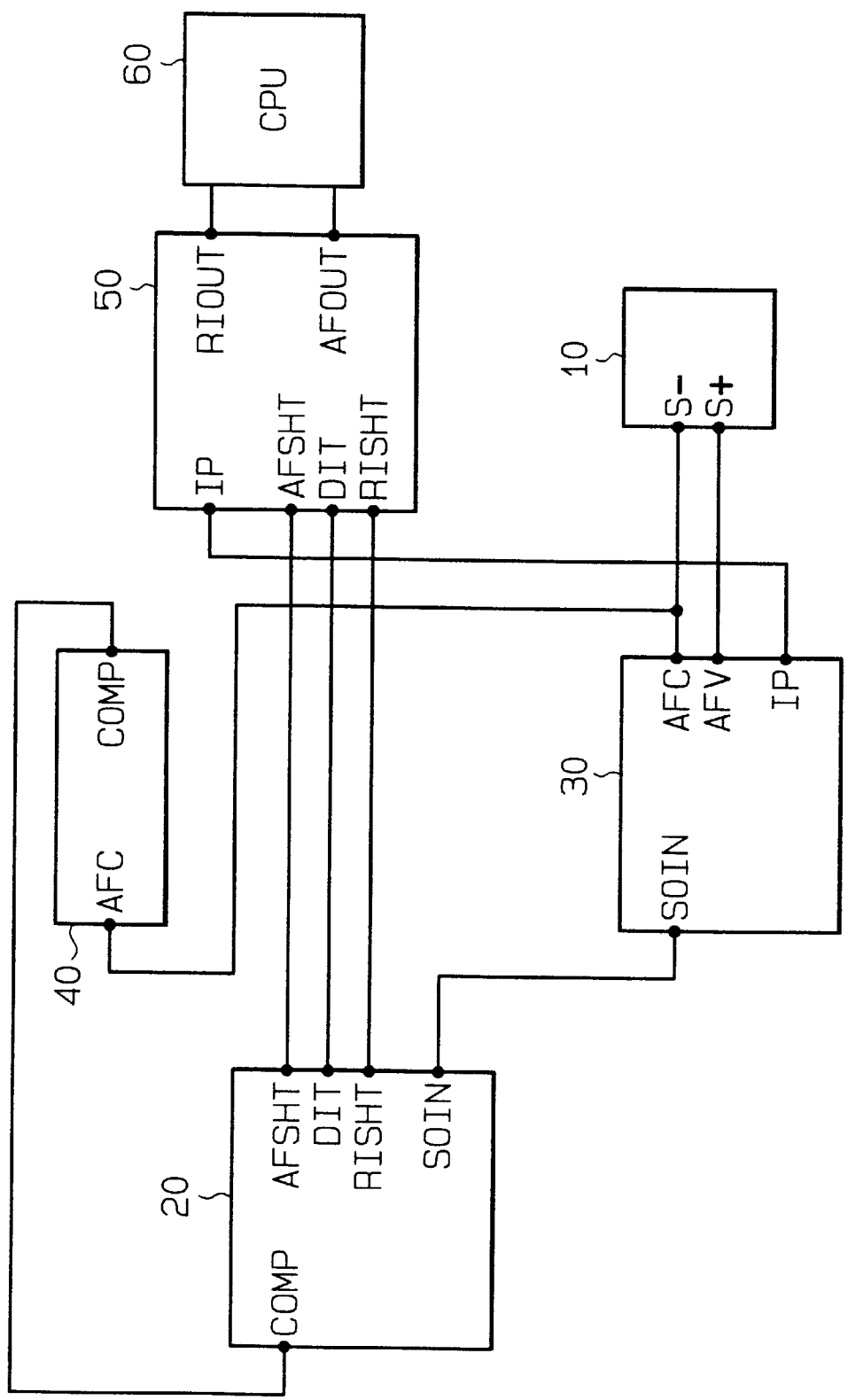
FIG. 1 is a schematic diagram showing an air-fuel ratio detection apparatus according to an embodiment of the present invention.

The above structure will be explained in detail hereinafter. FIG. 1 is a schematic diagram showing the air-fuel ratio detection sensor according to the present invention. As shown in FIG. 1, the air-fuel ratio detection sensor comprises an A/F ratio sensor 10, a timing decision circuit 20, a bias control circuit 30, a comparing circuit 40, a data output circuit 50 and a CPU 60.

The A/F ratio sensor 10 includes an element portion using a solid electrolytic layer and two terminals (i.e., negative terminal (S−) and positive terminal (S+)) and generates a sensor current related to the oxygen concentration in the exhaust gas when a given voltage is applied to the two terminals.

The timing decision circuit 20 decides the timings for the A/F ratio and the element resistance detection periods, and outputs command signals (e.g., AFSHT signal, RISHT signal, DIT signal and SOIN signal) to the above-mentioned circuits. Here, the AFSHT signal is for commanding a timing to update or hold the A/F ratio, the RISHT signal is for commanding a timing to update or hold the element resistance, the DIT signal is also for commanding a timing to update or hold the element resistance, and is an inverted signal of the RISHT signal, the SOIN signal is for commanding a timing to apply an element resistance detection voltage to the A/F ratio sensor 10.

Each of the above signals is formed by a binary signal having both a high level and a low level. Here, the high level corresponds to a power supply voltage Vcc (5V), while the low level corresponds to a ground voltage (0V).

The bias control circuit 30 is provided to apply voltages AFC, AFV to the A/F ratio sensor 10 and to detect the current flowing in the A/F ratio sensor. Normally, the bias control circuit 30 applies an A/F detection voltage to the A/F ratio sensor 10, then detects the current, and outputs a sensor current signal IP which is related to the detected current. When the SOIN signal from the timing decision circuit 20 is input, the bias control circuit 30 switches the applied voltage from the A/F detection voltage to an element resistance detection voltage with a given time constant, and then detects the sensor current flowing at that timing and outputs it as the sensor current signal. Here, the bias control circuit 30 outputs the current corresponding to the A/F ratio and the current corresponding to the element resistance alternately as the sensor current signal IP.

The comparing circuit 40 inputs the voltage AFC, which is the voltage applied to the one terminal (S−) of the A/F ratio sensor 10, and compares the voltage AFC and a given reference voltage. Then the comparing circuit 40 outputs the comparing result to the timing decision circuit 20 as an output voltage COMP.

The data output circuit 50 divides the sensor current signal IP into two signals which correspond to the A/F ratio and the element resistance, respectively, based on the AFSHT signal, the RISHT signal and the DIT signal from the timing decision circuit 20. In other words, since the sensor current signal IP alternately represents the A/F ratio and the element resistance, the data output circuit 50 outputs an AFOUT signal corresponding to the A/F ratio and a RIOUT signal corresponding to the element resistance.

The CPU 60 inputs two output signals (AFOUT, RIOUT) from the data output circuit 50. The CPU detects the A/F ratio based on the AFOUT signal, and the element resistance based on the RIOUT.

Figure 2:
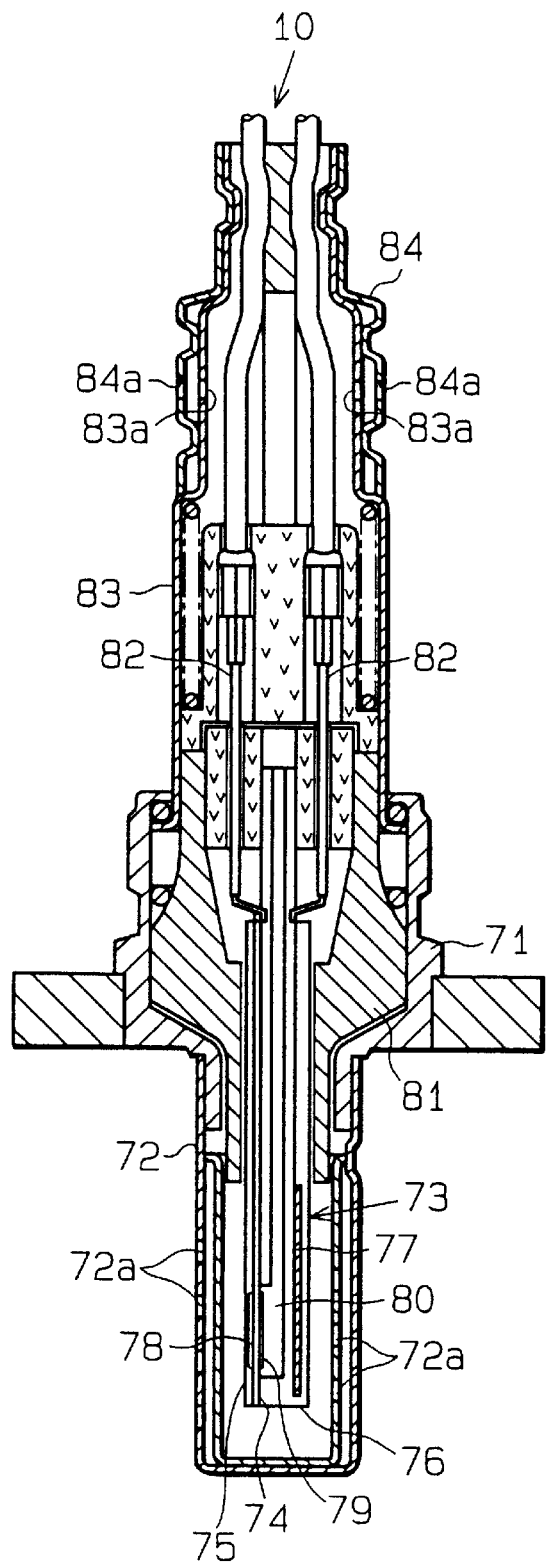
FIG. 2 is a sectional view showing the A/F ratio sensor.

Next, each of the above circuits is explained in detail. As shown in FIG. 2, the A/F ratio sensor 10 includes a cylindrical metal housing 71 fastened to an exhaust pipe wall of the engine. An element cover 72 is provided at a lower portion opening of the housing 71 and is formed by two plates, each of which has a bottom wall and a plurality of exhaust gas holes 72a, respectively.

A sensor element portion (cell) 73 includes mainly a solid electrolytic layer 74, a gas diffusion resistance layer 75, an air introduction duct 76 and a heater 77. Each of the above members 74–77 are formed by a rectangular plate, and are laminated together. A tip of the sensor element 73 is provided in the element cover 72. The solid electrolytic layer 74 is formed as a rectangular plate and is made from a partially stabilized zirconia sheet. A measure electrode 78 and an air side electrode 79, which are both made of platinum or the like, are provided on both sides of the solid electrolytic layer 74. Here, the measure electrode 78 and the air side electrode 79 are electrically connected to the two terminals of the A/F ratio sensor 10 (i.e., S−, S+terminals in FIG. 1), respectively.

The air introduction duct 76 is made of high heat conductivity ceramic such as an alumina. An air room 80 is formed from the air introduction duct 76. The air introduction duct 76 introduces air to the air side electrode 79 in the air room 80.

The sensor element portion 73 extends upwardly in FIG. 2 so as to penetrate a insulator 81 provided in the housing 71. A pair of lead wires 82 are connected on the top of the sensor element portion 73. A main cover 83 is fixed on the top of the housing 71 via caulking or the like, and in turn is covered by a dust cover 84. The upper portion of the sensor is protected by the main cover 83 and the dust cover 84. Each of the covers 83, 84 has a plurality of air holes 83a, 84a for introducing air into the inside of the covers 83, 84. Here, each of the air holes 83a, 84 are communicated to the air room 80 of the sensor element portion 73.

According to the A/F ratio sensor 10 constructed as described above, the sensor element portion 73 generates a limit current corresponding to the oxygen concentration in the region where the air-fuel ratio is on the lean side with respect to a stoichiometric air-fuel ratio value. While the sensor element portion 73 (the solid electrolytic layer 74) is capable of linearly detecting oxygen concentration, because the temperature required for activating the sensor element portion 73 is high (above 600° C.) and the temperature range for keeping the sensor element portion 73 active is relatively narrow, the heater 47 heats the sensor element portion so that the sensor element portion 73 can be kept in an activation temperature range. Meanwhile, when the air-fuel ratio is on the rich side with respect to the stoichiometric air-fuel ratio, the concentration of unburnt gas such as carbon monoxide (CO) or the like change substantially linearly relative to change in the air-fuel ratio, the sensor element portion 73 generates a limit current corresponding to the concentration of CO or the like.

The structure and its characteristic of the A/F ratio sensor 10 using the laminated structure described the above are described in detail in Japanese Patent Application, application serial No. Hei. 9-358524, and corresponding U.S. patent application, application Ser. No. 09/218,083, filed Dec. 22, 1998, "GAS COMPONENT CONCENTRATION MEASURING APPARATUS", the contents of both applications being incorporated herein by reference.

Figure 3:
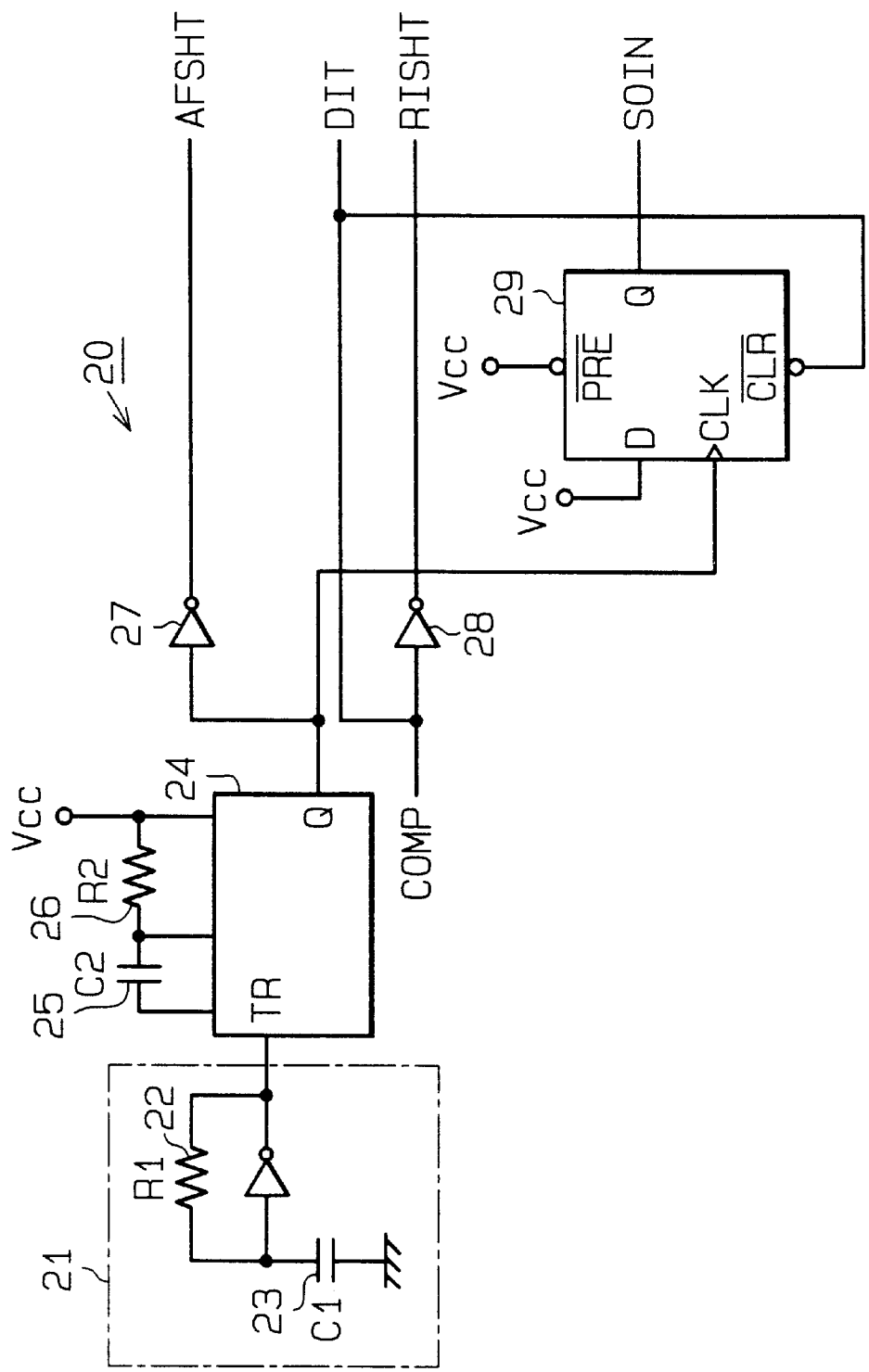
FIG. 3 is an electric circuit diagram showing a timing decision circuit.

FIG. 3 is a schematic circuit diagram showing the structure of the timing decision circuit 20 in detail. As to the timing decision circuit 20 shown in FIG. 3, an oscillator 21, which is for outputting a continuous square wave signal, includes a resistor 22 and a capacitor 23. The oscillator 21 decides its oscillation frequency based on a resistance R1 of the resistor 22 and a capacitance C1 of the capacitor 23. The oscillation frequency f is determined by the following equation:

$$f=1/(2 \times R1 \times C1 \times \ln 2)$$

In this embodiment, the oscillation frequency is determined substantially 1–10 Hz based on an interval of the element resistance detection.

An output of the oscillator 21 is input to a one-shot pulse circuit 24. The one-shot pulse circuit 24 outputs a pulse wave signal (one-shot pulse signal) having a predetermined pulse width when a rising trigger is input to a TR terminal. The pulse width is determined so that the element resistance can be detected during each pulse, and is determined based on a capacitance C2 of a capacitor 25 and a resistance R2 of a resistor 26 (i.e., pulse width=C2×R2). Specifically, the pulse width is set substantially in the range of several tens of microseconds.

The one-shot pulse signal is output as the AFSHT signal after passing through an inverter 27. In other words, an inverted signal of the output from the one-shot pulse 24 is the AFSHT signal.

The output voltage COMP itself from the comparing circuit 40 is output as the DIT signal, while the output voltage COMP is output as the RISHT signal after passing through an inverter 28. In other words, the RISHT signal is a logically inverted signal with respect to the DIT signal (output voltage COMP).

The one-shot pulse signal (output of the one-shot pulse circuit 24) is input to a D-type flip-flop 29. The flip-flop 29 outputs the SOIN signal (the signal for commanding a timing to apply an element resistance detection voltage) with respect to the input signal. Specifically, a D terminal of the flip-flop 29 inputs the power supply voltage Vcc, a clock input terminal (CLK) inputs the one-shot pulse signal and a clear terminal (CLR: here, the top line indicates logical inversion) inputs the a logically inverted DIT signal.

In this structure, the flip-flop 29 changes the output (Q) to a logically high level (i.e., changes the SOIN to a logically high level) when the one-shot pulse signal rises. The flip-flop 29 change the output (Q) to a logically low level (i.e., change the SOIN to a logically low level) when the one-shot pulse signal falls. In other words, since the D terminal is always a logically high level, the output (Q) is changed to a logically high level when the clock is input, and the output (Q) is returned to a logically low level when the DIT signal, which is input by the CLR terminal, is changed to a logically low level.

Figure 4:
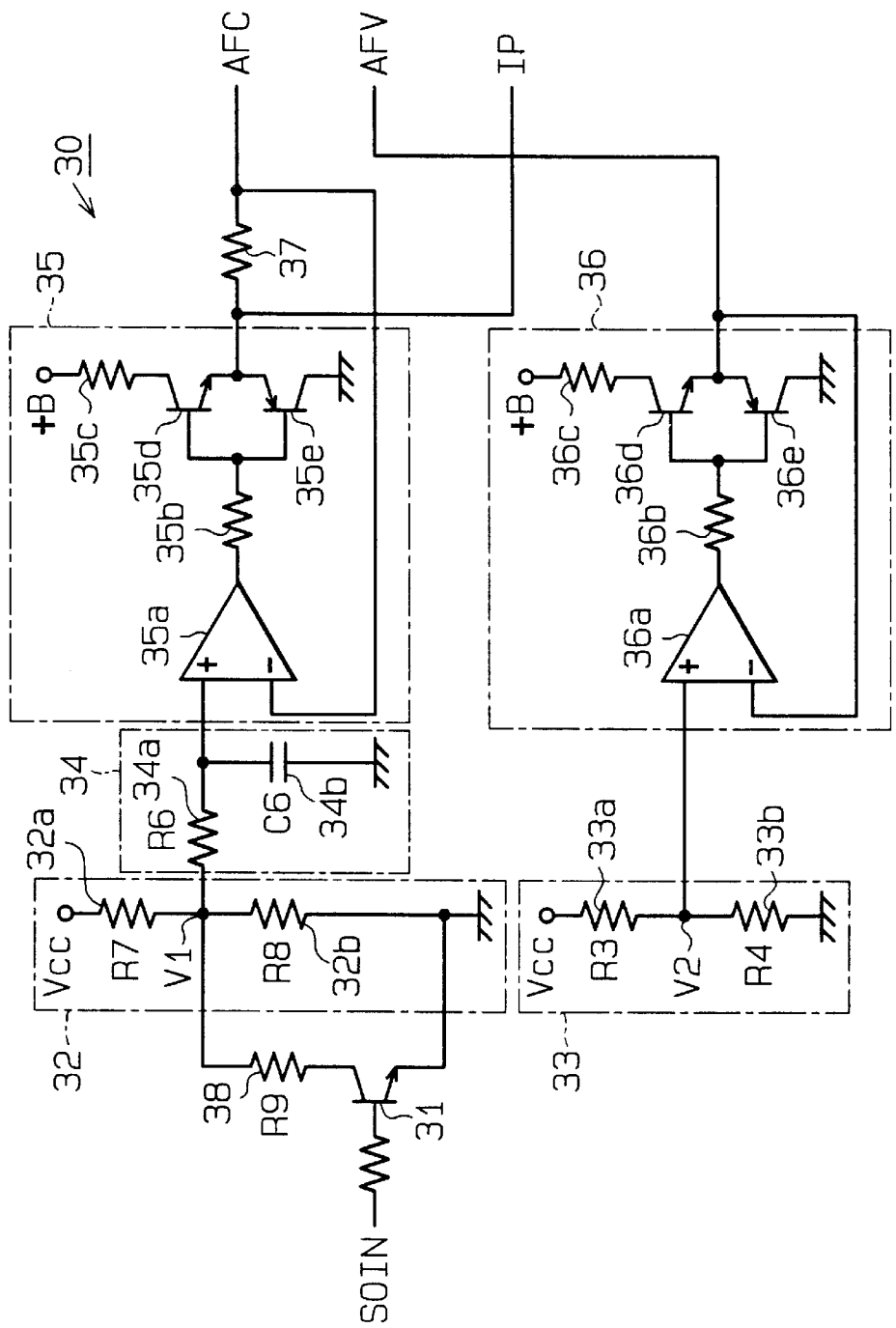
FIG. 4 is an electric circuit diagram showing a bias control circuit.

FIG. 4 is a schematic circuit diagram showing the structure of the bias control circuit 30 in detail. The bias control circuit 30 includes mainly a transistor 31 to input the SOIN signal from the timing decision circuit 20 to its base terminal, reference voltage circuits 32, 33 to generate voltages V1, V2 which are input to the A/F ratio sensor 10, a low pass filter 34 to round the voltage V1 with a given time constant, a pair of voltage follower circuits 35, 36 and a current detection resistor 37 to detect the sensor current (IP).

The reference voltage circuit 32 includes resistors 32a, 32b to divide the power supply voltage Vcc. When resistance of the resistors 32a, 32b are R7, R8, respectively, the voltage V1 which is the voltage of a dividing point by the above resistors is represented by the following equation:

$$V1=\{R8/(R7+R8)\} \times Vcc$$

The reference voltage circuit 33 includes resistors 33a, 33b to divide the power supply voltage Vcc. When resistance of the resistors 33a, 33b are R3, R4, respectively, the voltage V2 which is the voltage of a dividing point by the above resistors is represented by the following equation:

$$V2=\{R4/(R3+R4)\} \times Vcc$$

The low pass filter 34 includes a resistor 34 and a capacitor 34b. When the resistance of the resistor 34a is R6, a capacitance of the capacitor 34b is C6, a time constant τ is determined by the following equation:

$$\tau=1/(2 \times \pi \times R6 \times C6)$$

Here, when a cutoff frequency is set to substantially 40 Hz, the time constant of the low pass filter is determined to be smaller than an inverse of the cutoff frequency.

The voltage follower circuit 35 includes an operational amplifier 35a, resistors 35b, 35c and transistors 35d, 35e. An output of the voltage follower circuit 35 is applied to one terminal (negative terminal S– in FIG. 1) of the A/F ratio sensor 10 via the current detection resistor 37.

The voltage follower circuit 36 includes an operational amplifier 36a, resistors 36b, 36c and transistors 36d, 36e. An output of the voltage follower circuit 36 is applied to another terminal (positive terminal S+ in FIG. 1) of the A/F ratio sensor 10.

Therefore, when the SOIN signal is at a logically low level, the transistor turns off. Here, a difference between the voltages V1, V2, which are generated in the power supply circuits 32, 33 (V2–V1) is applied to the A/F ratio sensor. Actually, a constant voltage having substantially several hundreds millivolts is applied to the A/F ratio sensor.

When the SOIN signal is switched to a logically high level, the transistor 31 will turn on. Here, the voltage V1 is changed from the described value, that is $$\{R8/(R7+R8)\} \times Vcc$$

to a square wave voltage represented by the following equation:

$$\{R8 \times R9/(R7 \times R8 + R8 \times R9 + R9 \times R7)\} \times Vcc$$

Here, R9 is a resistance of the resistor 38. When the voltage V1 is changed as shown above, the voltage wave is rounded with time constant of the low pass filter 34, and the rounded voltage AFC is applied to the one terminal of the A/F sensor.

As mentioned above, when the voltage is applied to the A/F sensor 10, a current is generated in the A/F ratio sensor 10. The current is detected by the current detection resistor 37 by means of a detected voltage value, and the detected value is output from the bias control circuit 30 as the sensor current signal IP.

FIG. 5 is a schematic circuit diagram showing the structure of the comparing circuit 40 in detail. In FIG. 5, a comparator 41 inputs the voltage AFC from its positive terminal (+), and inputs the reference voltage Vref which is generated from power supply voltage Vc and resistors 42, 43 from its negative terminal (−). The comparator 41 compares the applied voltage AFC and the reference voltage Vref, and sets the output voltage COMP to a logically low level when the applied voltage AFC is higher than the reference voltage Vref, and sets the output voltage COMP to a logically high level when the applied voltage AFC is lower than the reference voltage Vref.

When the transistor 31 shown in FIG. 4 is switched from OFF to ON, the voltage V1 of the dividing point in the reference voltage circuit 32 change by a certain amount of change. The reference voltage is determined so that an amplitude of the reference voltage is smaller than the amount of change. In other words, when the voltage difference ΔV, which is the difference between the voltage V1 and the reference voltage Vref when the transistor 31 in FIG. 4 is OFF, and the amount of change $V_0$ of the voltage V1 when the transistor 31 is switched from OFF to ON, are compared, the following relationship exists:

$$\Delta V < V_0$$

Actually, the voltage difference ΔV between the voltage V1 and the reference voltage Vref when the transistor 31 in FIG. 4 is OFF may be range from several tens of millivolts to several hundred millivolts.

The output of the comparator 41 is electrically connected to a base of a transistor 45 via resistor 44. A collector and an emitter of the transistor 45 are connected via resistor 46. Therefore, when resistance of the resistors 42, 43, 46 are R10, R11, R12, respectively, and when the output voltage COMP is at a logically high level and the transistor 45 is ON, the reference voltage Vref is represented by the following equation:

$$Vref = \{R11/(R10+R11)\} \times Vcc$$

When the output voltage COMP is at a logically low level and the transistor 45 is OFF, the reference voltage Vref is represented by the following equation:

$$Vref = \{(R11+R12)/(R10+R11+R12)\} \times Vcc$$

Here, the reference voltage Vref when the transistor 45 is OFF is higher than the reference voltage Vref when the transistor 45 is ON. In other words, the reference voltage has a hysteresis with respect to the output of the comparator 41. Therefore, the output of the comparator is stable.

Figure 6:
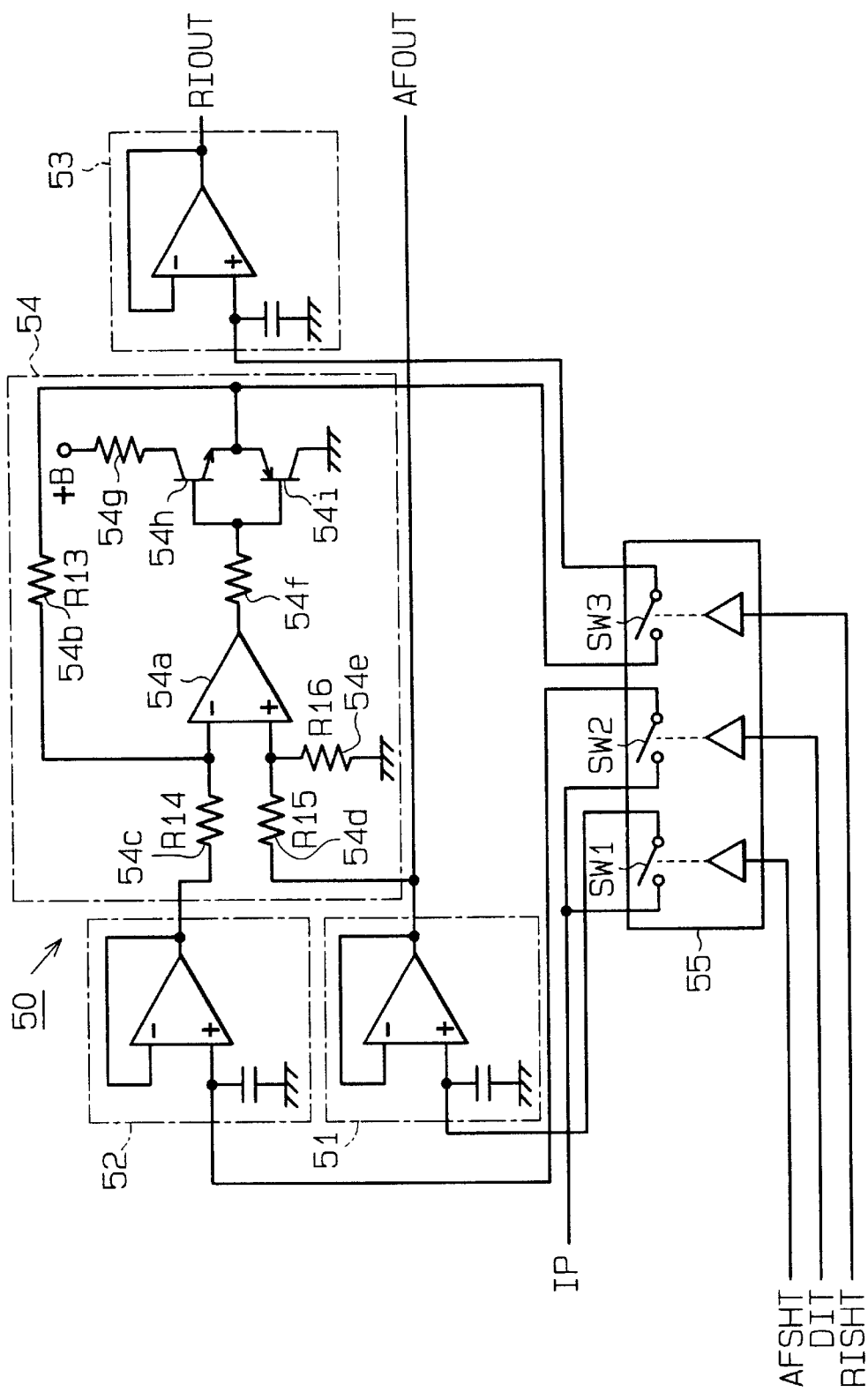
FIG. 6 is a schematic circuit diagram showing the structure of the data output circuit.

FIG. 6 is a schematic circuit diagram showing the structure of the data output circuit 50 in detail. The data output circuit 50 includes mainly sample hold circuits 51, 52, 53, a differential amplifier circuit 54 and an analog switch circuit 55. The sample hold circuits 51–53 are each formed by a combination of an operational amplifier and a capacitor.

The differential amplifier circuit 54 includes an operational amplifier 54a, resistors 54b–54g and transistors 54h, 54i. The operational amplifier 54a receives an output of the sample hold circuit 51 from its positive terminal (+) via resistor 54d, and an output of the sample hold circuit 52 from its positive terminal (−) via resistor 54c. Here, the differential amplifier circuit 54 outputs a signal related to the difference voltage between output of the sample hold circuit 51, 52. When a resistance of resistors 54b–54e are R13, R14, R15, R16, respectively, an amplification factor of the differential amplifier circuit 54 is represented as R13/R14 (=R16/R15). This amplification factor is determined with respect to a range of the CPU (engine control circuit) which receives the output RIOUT signal.

The analog switch circuit 55 includes switches SW1, SW2, SW3. The switch SW1 turns ON/OFF with respect to the AFSHT signal which is received from the timing decision circuit 20. When SW1=ON, the sensor current signal IP is supplied to the sample hold circuit 51. The switch SW2 also turns ON/OFF with respect to the DIT signal received from the timing decision circuit 20. When SW2=ON, the sensor current signal IP is supplied to the sample hold circuit 52. The switch SW3 also turns ON/OFF with respect to the RISHT signal received from the timing decision circuit 20. When SW3=ON, the output of the differential amplifier current 54 is supplied to the sample hold circuit 53.

In this case, when the switches are ON (each of the AFSHT signal, DIT signal, RISHT signal is at a logically high level), each of the sample hold circuits 51–53 updates the held value with the input terminal voltage. When the switches are OFF (each of the AFSHT signal, DIT signal, RISHT signal is a logically low level), each of the sample hold circuits 51–53 holds the value updated last time. The output of the sample hold circuit 51 is output as the AFOUT signal corresponding to the A/F ratio at each timing interval. The output of the sample hold circuit 53 is output as the RIOUT signal corresponding to the element resistance at each timing interval.

Operation of the data output circuit 50 will be explained briefly hereinafter. When the AFSHT signal is at a logically high level, since the switch SW1 turns on, the sample hold circuit 51 outputs the sensor current signal IP itself as the AFOUT signal. Here, when the RISHT signal is at a logically low level, the sample hold circuit 53 does not update its output (RIOUT signal) but rather holds the last value, independent of the logical level of the DIT signal.

When the switch SW1 turns off by setting the AFSHT signal to a logically low level, the sample hole circuit 51 holds the sensor current signal IP which is output just before the SW1 is turned off. Here, when the DIT signal is at a logically high level, the sample hold circuit 52 outputs the sensor current signal IP itself.

When the switch SW2 turns off by setting the DIT signal to a logically low level, the sample hold circuit 52 holds the sensor current signal IP output just before the SW2 is turned off. In this case, the differential amplifier circuit 54 outputs a current in proportion to the difference between the sensor current signal IP, which is held by the sample hold circuit 51 just before the switch SW1 turns off, and the sensor current signal IP, which is held by the sample hold circuit 52 just before the switch SW2 turns off. In response to the switch SW3 being turned off by the RISHT signal being set to a logically high level, the output of the differential amplifier circuit 54 is supplied to the sample hold circuit 53 via the switch SW3. Then, the sample hold circuit 53 updates the held value, and outputs the updated value as the RIOUT signal.

The switch SW3 turns off by setting the RISHT signal to a logically low level, then the sample hold circuit 53 holds the value which is output just before the SW3 is turned off. In this way, the data output circuit 50 alternately outputs the AFOUT signal and the RIOUT signal based on the temporally continuous sensor current signal IP.

Operation of the air-fuel ratio detection apparatus constructed as described above will be explained hereinafter with reference to FIGS. 7A–7B and 8A–8I.

FIG. 7A shows the waveform of the output from the oscillator 21 in the timing decision circuit 20. FIG. 7B shows the waveform of the output from the one-shot pulse circuit 24 in the timing decision circuit 20. As shown FIGS. 7A, 7B, the oscillator outputs the square wave signal at a given cycle, the one-shot pulse circuit 24 outputs the pulse signal having a predetermined pulse width (pulse width is in the range of several tens of microseconds) when the square wave signal rises.

FIGS. 8A–8I are timing diagram for explaining the signal wave from each of the circuits in detail. In FIGS. 8A–8I, a period t1–t4 corresponds to one pulse from the one-shot pulse circuit 24 in FIGS. 7A, 7B. This period t1–t4 corresponds to the period needed for the element resistance detection of the A/F ratio sensor 10.

In FIGS. 8A–8I, in the A/F ratio detection period that precedes time t1, each of the AFSHT, COMP, DIT, RISHT and SOIN signals are held at certain logical levels shown in FIGS. 8A–8I, respectively.

In other words, in the timing decision circuit 20 shown FIG. 3, the AFSHT signal, which is the inverse signal of output from the one-shot pulse circuit 24, is set to a logically high level while the pulse signal is not output from the one-shot pulse circuit 24. Here, because AFC>Vref, the output voltage COMP from the comparing circuit is set to a logically high level, the DIT signal, which is same signal as the COMP, is set to a logically high level, and the RISHT signal, which is inverse signal of the COMP, is set to a logically low level.

Now, since the SOIN signal is at a logically low level, the voltage of the dividing point shown in FIG. 4 is held by the following equation:

$$V1 = \{R8/(R7+R8)\} \times Vcc$$

When the voltages AFC, AFV are applied to terminals of the A/F ratio sensor 10, the sensor element portion 73 (solid electrolytic layer 74) generates the limit current, which is related to the oxygen concentration in the exhaust gas, and the limit current is measured by the bias control circuit 30 as the sensor current signal IP.

In this situation, regarding the data output circuit 50 shown in FIG. 6, because SW1=ON, SW2=ON, SW3=OFF, the sample hold circuit 51 outputs the sensor current signal IP itself as the AFOUT signal to the CPU 60. The CPU 60 detects the A/F ratio based on the AFOUT signal (sensor current signal IP).

At time t1, the one-shot pulse circuit 24 outputs the pulse signal, and the AFSHT signal, which is the inverse signal of the pulse signal, is changed to a logically low level. At the same time, the SOIN signal is changed to a logically low level. As to the data output circuit shown in FIG. 6, the switch SW1 turns from ON to OFF, the sample hold circuit 51 holds "IP1" which is the sensor current signal IP at time t1.

At time t1, regarding the bias control circuit 30 shown in FIG. 4, the voltage V1 of the dividing point in the reference voltage circuit 32 change by the following equation:

$$\{R8 \times R9/(R7 \times R8 + R8 \times R9 + R9 \times R7)\} \times Vcc$$

When the applied voltage AFC change in proportion to the voltage V1, the waveform of the voltage AFV is rounded with a given time constant. In other words, from time t1 to time t2, the voltage AFV applied to the A/F ratio sensor change due to rounding with a given time constant (gradually decreases, as shown in figure).

Here, since the DIT signal is held at a logically high level (SW2=ON), the sample hold circuit 52 outputs the sensor current signal, which change as shown in FIGS. 8A–8I, itself.

As to the comparing circuit 40 shown in FIG. 5, the output voltage COMP change to a logically low level due to the operation of the comparator 41, when the applied voltage AFC becomes lower than the reference voltage Vref (time t2). Here, the reference voltage Vref is determined so that the difference between the reference voltage Vref and the applied voltage AFC (ΔV) is smaller than the amount of change of the voltage V1 in the reference voltage circuit 32 (i.e., ΔV=several tens of millivolts–several hundred millivolts). When the output voltage COMP is switched from high to low, since the transistor 45 shown in FIG. 5 turns off, a current flows in the resistor 46, and the reference voltage is increased.

At time t2, the DIT signal is changed to a logically low level, the and switch SW2 in the data output circuit 50 (shown in FIG. 6) is switched from ON to OFF. Hence, the sample hold circuit 52 holds "IP2" which is the sensor current signal IP at time t2. The current IP2 corresponds to an amount of current change ΔI with respect to the current IP1.

Here, since the sample hold circuit 51 holds the current IP1 and the sample hold circuit 52 holds the current IP2, the differential amplifier circuit 54 output a signal in proportion to the ΔI (=IP1–IP2). At time t2, since the switch SW3 turns on by setting the RISHT signal to a logically high level, the output (i.e., the value in proportion to the ΔI) of the differential amplifier circuit 54 is supplied to the sample hold circuit 53, and the capacitor of the sample hold circuit is charged by the supplied output. In other words, the sample hold circuit 53 updates the held value, and outputs the updated value to CPU 60 as the RIOUT signal.

The CPU inputs the updated RIOUT signal, and detects the element resistance based on the amount of voltage change ΔV and the amount of current change ΔI (the element resistance=ΔV/ΔI).

Furthermore, at time t2, since the DIT signal, which is input to the CLR terminal of the flip-flop 29 in the timing decision circuit 20 (FIG. 3), is changed to a low level, the SOIN signal is switched to a logically low level. Hence, the voltage V1, which is the voltage of the dividing point in the reference voltage circuit 32 shown in FIG. 4 is determined by the following equation:

$$V1 = \{R8/(R7+R8)\} \times Vcc$$

Subsequently, at time t3, the voltage AFC applied to the A/F ratio sensor exceeds the reference voltage Vref, and the output voltage COMP is changed to a logically high level. At the same time, since the DIT signal is changed to a logically high level and the RISHT signal is changed to a logically low level, the switch SW2 turns from OFF to ON and the switch SW2 turns from ON to OFF. Therefore, after time t3, the sample hold circuit 53 holds the detected value (the value in proportion to ΔI) which is detected during time t2–t3. The sample hold circuit 52 outputs the sensor current signal IP itself.

Here, the period between the times t2, t3 corresponds to a minimum time needed to update the value of the sample hold circuit 53 in the data output circuit 50.

Then, at time t4, the pulse signal output from the one-shot pulse circuit 24 falls, and the AFSHT signal returns to a logically high level. As to the data output circuit 50 shown in FIG. 6, since the SW1=ON, the sample hold circuit 51 outputs the sensor current signal IP itself to the CPU as the AFOUT signal. After time t4, CPU re-starts the A/F ratio detection based on the AFOUT signal (sensor current signal IP).

As described above, the procedure of the embodiment detects an amount of current change ΔI before the voltage, which has the given time constant, converges to the constant value $V_0$.

Turning now to FIGS. 12–14, a mechanism that the element resistance can be detected based on voltage and current changes, which are measured before the convergence, will be explained hereinafter with reference to FIGS. 12–14. Further, a mechanism that this detection procedure can detect the element resistance accurately even if the time constant fluctuates will now be explained.

Here, a gas concentration sensor using a solid electrolytic can be represented by an equivalent circuit shown in FIG. 12. In the equivalent circuit, particle resistance of the solid electrolytic layer against oxygen ion is indicated by Rg, particle resistance and intergranular capacitance of the solid electrolytic layer in its granular interface are indicated by Ri and Ci, respectively, and electrode interface resistance and electrode interface capacitance are indicated by Rf and Cf, respectively. The equivalent circuit in FIG. 12 is simplified as an equivalent circuit shown in FIG. 13A. This simplification is based on the fact that, since the voltage Vc actually applied to the gas concentration sensor has a rising time constant of several kHz to several tens kHz, a current in FIG. 12 flows mostly through a path Rg-Ri-Cf. Therefore, the equivalent circuit of the sensor shown in FIG. 13A is simplified as a HPF (high pass filter) shown in FIG. 13B.

Furthermore, when a LPF (low pass filter) is employed as a circuit for outputting the voltage having the given time constant, a circuit configuration from the voltage applied to sensor current may be expressed as shown in FIG. 14. When a time constant of the LPF is "T2" and a convergence value of the voltage V is "$V_0$", the voltage V is expressed as a temporally delayed waveform with respect to rectangular wave by the following equation:

$$V = V_0 \times (1 - e^{-t/T2}) \qquad (1)$$

When a time constant of the HPF, which is a cutoff frequency of the sensor characteristic, is "T1", a current waveform I is expressed by the following equation:

$$I = (V_0/R) \times \{T1/(T1-T2)\} \times (e^{-t/T1} - e^{-t/T2}) \qquad (2)$$

Hence, based on the above equations (1), (2), the voltage ΔV and the current ΔI at time tTH are expressed by the following equations:

$$\Delta V = V_0 \times (1 - e^{-tTH/T2}) \qquad (3)$$

$$\Delta I = (V_0/R) \times \{T1/(T1-T2)\} \times (e^{-tTH/T1} - e^{-tTH/T2}) \qquad (4)$$

The element resistance is expressed by the following equation:

$$\Delta V/\Delta I = \{(T1-T2)/T1\} \times \{(1-e^{-tTH/T2})/(e^{-tTH/T1} - e^{-tTH/T2})\} \times R \qquad (5)$$

Here, in equation (5), since the time constant T1 corresponding to the cutoff frequency of the gas concentration sensor is much larger than the time constant of the LPF T2 or tTH (i.e., voltage change time), the first and second terms of equation (5) can be approximated by the following equations:

$$(T1-T2)/T1 \approx 1 \qquad (6)$$

$$(1-e^{-tTH/T2})/(e^{-tTH/T1} - e^{-tTH/T2}) \approx 1 \quad (\because e^{-tTH/T1} \approx 1) \qquad (7)$$

Therefore, equation (5) is simplified by the following equation:

$$\Delta V/\Delta I \approx R \qquad (8)$$

Equation (8) shows that the element resistance R can be detected based on the amount of voltage change ΔV measured before this voltage converges and the corresponding amount of current change ΔI.

In each equation, since both ΔV and $V_0$ are constant, a ratio of tTH and T2 is kept constant based on the equation (3). Consequently, a value of the equation (7) does not change. As to the equation (6), a value of the equation (6) does not change even if T1 fluctuates within tenths of a percentage. Then a value of the equation does not change. Based on the above, the detection procedure according to the present invention can detect the element resistance accurately even if some parameters, such as the time constant or the detection timing of current change due to the voltage change, fluctuates.

Furthermore, since this apparatus is formed by electric circuits (i.e., the comparing circuit 40 as "first circuit", the timing decision circuit 20 as "second circuit", and the data output circuit 50 as "third circuit"), the timing at which the amount of the voltage change reaches the given value can be detected accurately. In other words, in an engine control microcomputer (i.e., engine control ECU), operation programs as well as various other programs are executed at a given cycle. Therefore, the detection timing of the voltage change and the current change may fluctuate at least 10 μs, and detected element resistance may include some errors. On the other hand, according to this embodiment, the voltage change and the current change can be detected instantly at a desired timing, and fluctuation of the detection timing of the voltage change and the current change can be decreased substantially. Consequently, the element resistance can be detected accurately. Furthermore, since the voltage change and the current change are instantaneously detected, period during which detection of the gas concentration (i.e., A/F) is impossible is decreased.

According to the above-described embodiment, following merits can be further obtained.

Figure 9A:
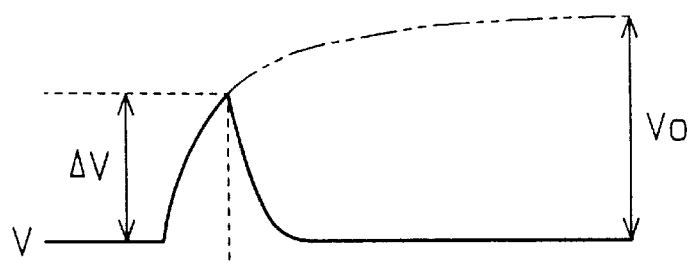
FIGS. 9A, 9B are waveform diagrams illustrating voltage change and current change at the time of element resistance detection.
Figure 9B:
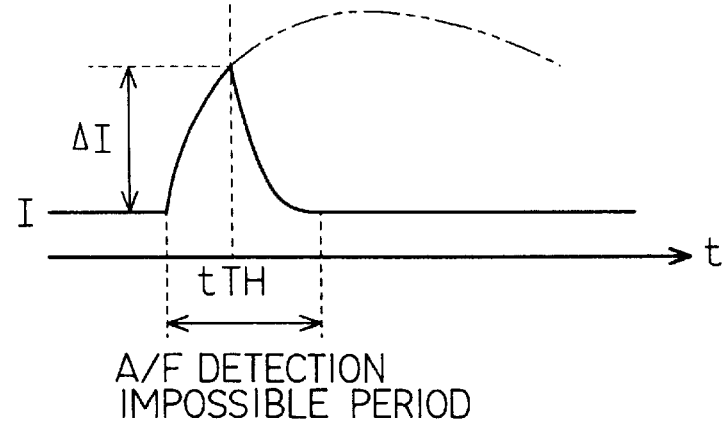
Figure 10A:
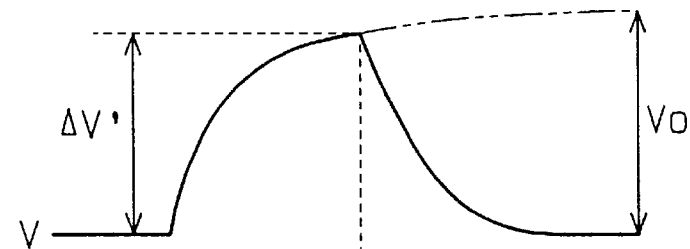
FIGS. 10A, 10B are waveform diagrams illustrating voltage change and current change at the time of element resistance detection.
Figure 10B:
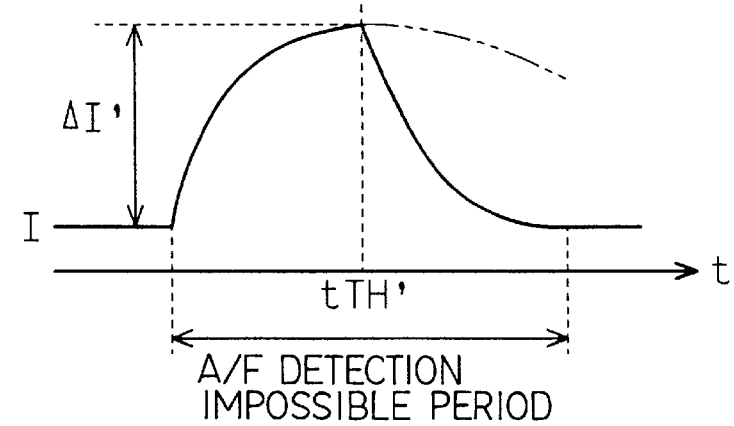

(a) In this embodiment, the voltage change and the current change are detected when the applied voltage, which change with the given time constant, reaches the given reference voltage Vref. In other words, as shown in FIGS. 9A and 9B, the amount of the current change ΔI of the sensor current is detected before the voltage, which change with the given time constant, converges to the voltage $V_0$.

As shown in FIGS. 11A and 11B, when the time constant for changing the applied voltage fluctuates, time to reach the peak current ΔI' also fluctuates. Therefore, the conventional procedure, represented by the two-dot chain line, that detects the current at the given time "tTH'" may cause fluctuation of detected current "ΔI'". On the other hand, as to the present embodiment, since the current ΔI is detected at time the applied voltage reaches the given value (i.e., ΔV in FIG. 11A), the current ΔI is detected accurately even if the time constant fluctuates. Since detected current ΔI does not include any fluctuation, accuracy of the element resistance detection can be increased.

Specifically, the voltage and current changes are detected when the amount of the voltage change reaches a threshold voltage. Here, the threshold voltage is determined to be smaller than a command voltage that detects the change timing of the applied voltage from the gas concentration detection voltage to the element resistance detection voltage. According to the above procedure, since the voltage and current changes are detected before the sensor current reaches the peak, a total time for detecting the element resistance can be decreased (see FIG. 11).

(b) Furthermore, as shown in FIGS. 9A, 9B, 10A, 10B, 11A and 11B, since the time "tTH" is shorter than the time "tTH'", a total detection time can be decreased. Therefore, a time period in which the gas concentration (e.g., A/F) cannot be detected (A/F detection impossible period) (i.e., a period from the timing the applied voltage is switched to an element resistance detection voltage to the timing the applied voltage is returned to a gas concentration detection voltage) is decreased. As a result, an influence on the gas concentration detection can be decreased.

When "tTH" is long, the left term in equation (7) is larger than the right term, i.e., "1". Then, based on the equation (5), detected element resistance is largely different from actual element resistance. In other words, the present invention can detect the element resistance accurately, compared to the conventional detection procedure that detects the element resistance at tTH' when the current reaches a peak, as described in Japanese Laid-open patent application No. Hei. 9-292364.

(c) The reference voltage Vref of the comparing circuit 40 exhibits hysteresis. Hence, the output of the comparator 41 is stable. Therefore, an adequate time needed to re-write the data at the update timing of RIOUT in the data output circuit 50 can be obtained.

(d) As to the air-fuel ratio detection apparatus, an electric circuit operates as follows:

detecting an amount of voltage change, which has a given time constant, reaches a given value, deciding a detection of voltage change and current change for an element resistance detection at the timing when the amount of the voltage change reaches the given value, and measuring the current change in relation to the voltage change at the timing when the amount of the voltage change reaches the given value.

According to the above circuit operation, fluctuation of the detection timing of the voltage and current changes can be decreased substantially, then the element resistance can be detected more accurately, compared to a structure which realizes the above procedure by an engine control microcomputer (engine control ECU) or the like. Furthermore, since the voltage and current changes are instantaneously detected, a period in which the gas concentration (i.e., A/F) cannot be detected can be decreased.

(e) Since the comparing circuit 40, the timing decision circuit 20, and the data output circuit 50 are formed by analog element circuits, the apparatus can also be realized at low cost.

(f) During the A/F ratio detection, the data output circuit 50 updates the detected AFOUT signal with keeping detected the RIOUT signal, which was previously detected. During the element resistance detection, the data output circuit 50 updates the detected RIOUT signal with keeping detected the AFOUT, which was previously detected. Here, the A/F ratio detection and the element resistance detection can be carried out continuously. And during either the gas concentration detection or the element resistance detection, the detected value of another detection can be held.

(g) The time constant of the low pass filter 34 is set to be smaller than an inverse of the cutoff frequency of the gas concentration sensor. In the case of a gas concentration sensor using a solid electrolytic layer, such as zirconia, when the time constant is set based on the cutoff frequency of the sensor, a voltage apply time in the element resistance detection can be set suitably without prolonging the process.

(h) Since the element resistance can be detected accurately, an activation control (power control of the heater) of the A/F ratio sensor based on the detected element resistance can be realized accurately. The detection result of the element resistance can be effectively adopted to a deterioration detection of the sensor 10.

(i) A period from the timing of the applied voltage with the given time constant is switched to the timing of when the voltage change and current changes are detected, and is set to be shorter than an order of the given time constant. Also the voltage and the current changes are detected during the voltage changing. Therefore, the present invention can detect the element resistance accurately.

The present invention can be also realized by following embodiment.

A period from when the voltage is changed with the given time constant to when the voltage and voltage changes are detected, is set shorter than an order of the time constant of the low pass filter. In this case, the voltage and current changes are detected during the voltage changing. Consequently, accuracy of the element resistor detection can be improved.

In the above embodiment, the analog circuits are employed to detect the element resistance. However, the present invention can be realized in another way. If the fluctuation of the detection timing of the voltage change and the current change can be canceled within a given tolerance level (at most, several microseconds), an electric control apparatus which employs a microcomputer or the like can also realize the present invention.

In the above embodiment, the gas concentration sensor is realized by the laminated structure A/F ratio sensor, however, it can be also realized by a cup type A/F ratio sensor. Furthermore, other gas concentration sensors can be used in place the A/F ratio sensor. Specifically, a gas concentration sensor for detecting a concentration of a specific constituent in a detected gas, such as NOx sensor for detecting the NOx in an exhaust gas, or a multi-type gas concentration sensor for detecting $O_2$ and NOx and so on in an exhaust gas may be used. When the NOx sensor or the multi-type gas concentration sensor is realized, the present invention may be adapted to a gas concentration detection apparatus using the sensor.

What we claimed is:

1. A method for detecting element resistance of a gas concentration sensor, the method comprising:

applying a transient voltage having a given time constant to the sensor element;

detecting current change in the sensor element caused by said transient voltage at a detection time during the transient phase which occurs substantially before the transient voltage converges to a constant value; and determining element resistance of the gas concentration sensor element based on the value of the transient voltage causing the value of the detected current change.

2. A method for detecting element resistance of a gas concentration sensor as in claim 1, wherein:

the detection is determined by a process that includes detecting a time when the value of the transient voltage reaches a predetermined threshold value, and said detecting current change includes detecting the current change at the detected time.

3. A method for detecting element resistance of a gas concentration sensor as in claim 2, wherein:

detecting the time includes setting the threshold value smaller than a command value that corresponds to changing the applied voltage from a gas concentration detection voltage to an element resistance detection voltage.

4. A method for detecting element resistance of a gas concentration sensor as in claim 1, wherein the time constant is smaller than the inverse of a gas concentration sensor cutoff frequency.

5. A method for detecting element resistance of a gas concentration sensor as in claim 1, wherein the period from when the applied voltage is switched to when the voltage and current changes are detected is shorter than the predetermined time constant.

6. A gas concentration detection apparatus for detecting element resistance of a gas concentration sensor, said apparatus comprising:

a power supply which produces a transient voltage having a predetermined time constant to the sensor element;

a first circuit configured to detect when said transient voltage having a predetermined time constant reaches a predetermined value during the transient phase which is smaller than a converged substantially quiescent value;

a second circuit configured to detect voltage change at the detection time by the first circuit; and a third circuit configured to detect the current change caused by the transient voltage in response to detection by the second circuit thereby permitting a determination of the resistance of the gas concentration sensor without waiting for the transient voltage to converge to a substantially quiescent value.

7. A gas concentration detection apparatus for detecting element resistance of a gas concentration sensor as in claim 6, wherein:

the first circuit sets a threshold value smaller than a command voltage that corresponds to changing the applied voltage from a gas concentration detection voltage to an element resistance detection voltage, and further comprising a comparing circuit to compare the transient voltage with the threshold value.

8. A gas concentration detection apparatus for detecting element resistance of a gas concentration sensor as in claim 6, wherein the third circuit updates a detected gas concentration with detected element resistance previously detected during gas concentration detection, and updates the detected element resistance with the gas concentration detected previously during an element resistance detection.

9. A gas concentration detection apparatus for detecting element resistance of a gas concentration sensor as in claim 6, wherein the first, the second and the third circuits are formed by analog element circuits.

10. In a method of detecting gas concentration by applying different voltages to a gas sensor element during successive gas concentration detection and element resistance detection cycles, the improvement comprising:

detecting a change in sensor element current caused by a transient in applied voltage during an element resistance detection cycle at a detection time that occurs during the transient phase substantially before the applied voltage reaches a substantially stable value; and using the detected changes in transient applied voltage and current values to determine gas sensor element resistance.

11. In an apparatus for detecting gas concentration by applying different voltages to a gas sensor element during successive gas concentration detection and element resistance detection cycles, the improvement comprising:

means for detecting a change in sensor element current caused by a transient in applied voltage during an element resistance detection cycle at a detection time that occurs during the transient phase substantially before the applied voltage reaches a substantially stable value; and means for using the detected changes in transient applied voltage and current values to determine gas sensor element resistance.

* * * * *